(12) United States Patent
Pereira et al.

(10) Patent No.: US 9,332,991 B2
(45) Date of Patent: May 10, 2016

(54) ADHESIVE ARTICLES CONTAINING A COMBINATION OF SURFACE MICROPATTERNING AND REACTIVE CHEMISTRY AND METHODS OF MAKING AND USING THEREOF

(71) Applicants: Massachusetts Institute of Technology, Cambridge, MA (US); The Brigham and Women's Hospital, Inc., Boston, MA (US)

(72) Inventors: Maria Jose M. N. Pereira, Lisbon (PT); Woo-Kyung Cho, Arlington, MA (US); Robert S. Langer, Newton, MA (US); Jeffrey M. Karp, Brookline, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 87 days.

(21) Appl. No.: 14/092,015

(22) Filed: Nov. 27, 2013

(65) Prior Publication Data
US 2014/0148846 A1 May 29, 2014

Related U.S. Application Data

(60) Provisional application No. 61/731,178, filed on Nov. 29, 2012, provisional application No. 61/731,509, filed on Nov. 30, 2012.

(51) Int. Cl.
| | | |
|---|---|---|
| *A61B 17/08* | (2006.01) | |
| *A61D 1/00* | (2006.01) | |
| *A61B 17/11* | (2006.01) | |
| *A61L 15/58* | (2006.01) | |
| *A61L 15/42* | (2006.01) | |

(Continued)

(52) U.S. Cl.
CPC ............... *A61B 17/11* (2013.01); *A61L 15/26* (2013.01); *A61L 15/42* (2013.01); *A61L 15/44* (2013.01); *A61L 15/58* (2013.01); *A61L 15/62* (2013.01); *A61L 15/64* (2013.01)

(58) Field of Classification Search
CPC ............... A61B 17/085; A61B 2017/006464; A61B 2017/0065; A61L 15/58
See application file for complete search history.

(56) References Cited

U.S. PATENT DOCUMENTS

2005/0201974 A1 9/2005 Schestopol
2011/0021965 A1* 1/2011 Karp et al. ............... 602/54

FOREIGN PATENT DOCUMENTS

WO 2009067482 5/2005
WO 2012030570 8/2012

OTHER PUBLICATIONS

Geim, et al., "Microfabricated adhesive mimicking gecko foot-hair". Nat Mater, 2(7):461-3 (2003).

(Continued)

*Primary Examiner* — Melanie Tyson
(74) *Attorney, Agent, or Firm* — Pabst Patent Group LLP

(57) ABSTRACT

Adhesive articles containing microtopography, such as microprotrusions, and a coating of adhesive glue, such an adhesive having known toxicity and/or tissue reactive functional groups are described herein. The articles described herein contain a substrate, a plurality of microfeatures, and an adhesive, such as an adhesive glue. The articles described herein exhibit a 90° pull off adhesion of at least about 1.5 N/cm$^2$. The articles described herein can contain less adhesive than when the adhesive is used alone without microtopography and yet exhibit equivalent adhesive strength with little or no toxicity or other adverse side effects (e.g., exothermic reaction).

28 Claims, 2 Drawing Sheets

(51) Int. Cl.
*A61L 15/44* (2006.01)
*A61L 15/62* (2006.01)
*A61L 15/64* (2006.01)
*A61L 15/26* (2006.01)

(56) References Cited

OTHER PUBLICATIONS

Jeong, et al., "Stretched Polymer Nanohairs by Nanodrawing", Nano Letters, 6(7):1508-1513 (2006).

Kandavilli, "Polymers in transdermal drug delivery systems". Pharma Tech., http://www.pharmtech.com/pharmtech/data/artici-estandard/pharmtech/192002/18600/article.pdf, (retrieved on Feb. 10, 2014).

Mizrahi, et al., "Tissue adhesives as active implants", Soft Tissue Biomechanical Modeling for Computer Assisted Surgery, Jan. 1, 2010, Springer Berlin Heidlberg, Berlin, 8:39-56 (2010).

Yurdumakan, et al., "Synthetic gecko foot-hairs from multiwalled carbon nanotubes", Chem. Commun. (Camb), (30):3799-801 (2005).

\* cited by examiner

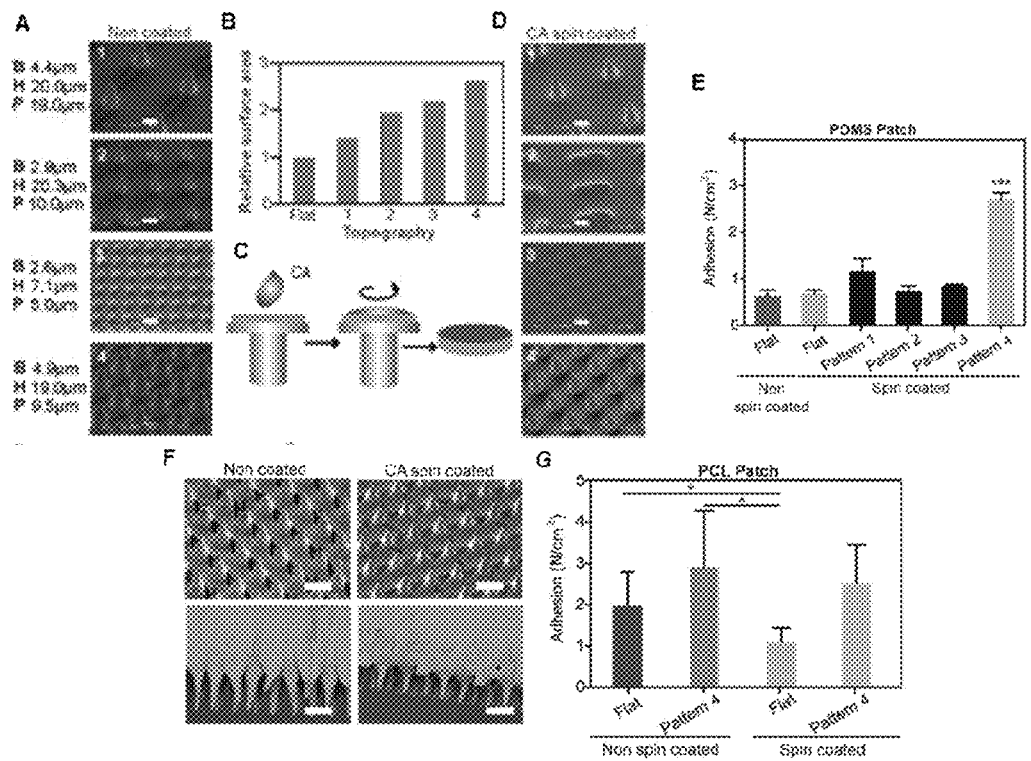
FIGS. 1A-G
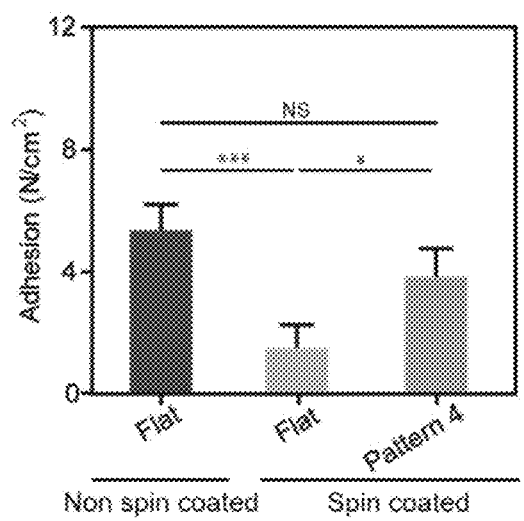
FIG. 2

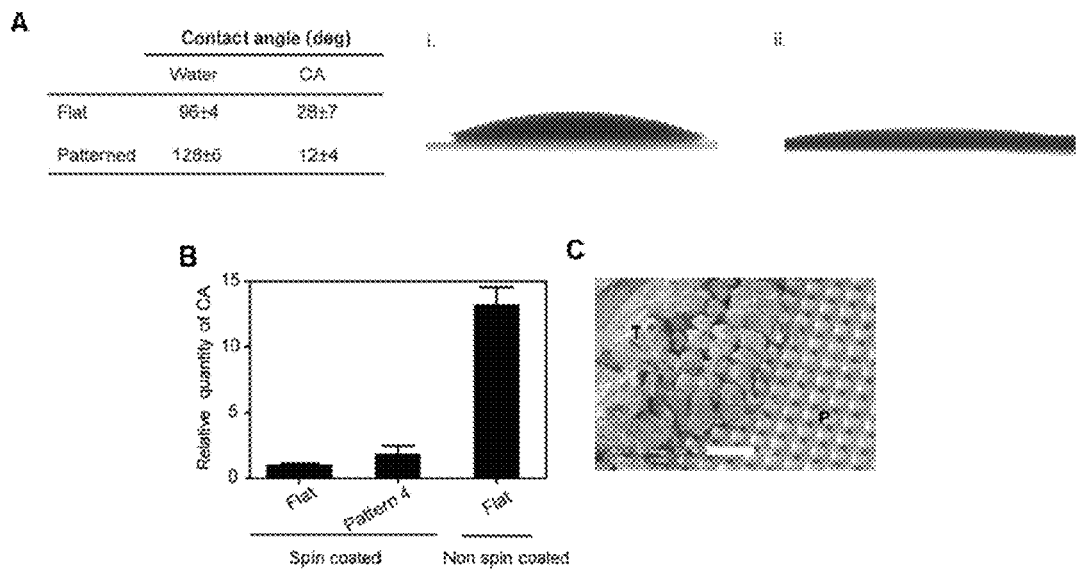
FIGS. 3A-3C
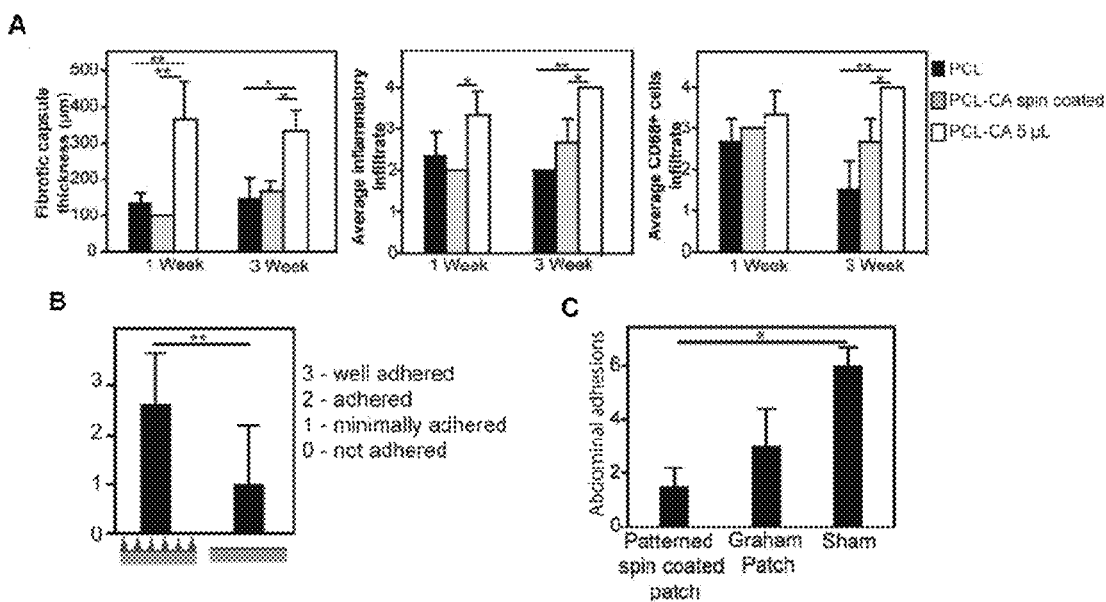
FIGS. 4A-C

ADHESIVE ARTICLES CONTAINING A COMBINATION OF SURFACE MICROPATTERNING AND REACTIVE CHEMISTRY AND METHODS OF MAKING AND USING THEREOF

CROSS-REFERENCE TO RELATED APPLICATIONS

This application claims the benefit of and priority to U.S. Ser. No. 61/731,178, filed Nov. 29, 2012 and U.S. Ser. No. 61/731,509, filed Nov. 30, 2012, all of which are incorporated herein by reference in their entirety.

FIELD OF THE INVENTION

This invention is in the field of adhesive articles, particular adhesive articles containing a combination of surface topography, such as micropatterning, and reactive chemistry.

BACKGROUND OF THE INVENTION

Sutures and staples are the main tissue attachment and closure techniques currently in use. However, these techniques can damage tissue due to deep piercing and expose it to tension forces that easily tear friable tissues. Suture application is also time-consuming and an invasive process, impeding the development of next generation, minimally invasive surgical procedures.

Biodegradable tissue adhesives for internal use offer a potential solution. These adhesives can be applied directly to a tissue surface and promote an immediate closure of an internal defect. However, the introduction of this approach into the clinic has been challenging given the lack of materials that can promote strong wet adhesion without exacerbated inflammatory and/or toxic responses.

Medical grade cyanoacrylates (CA) adhere strongly to tissue upon exposure to water or other basic compounds. Despite several attempts to improve its performance and biocompatibility through changes in the CA monomers chemical composition, however, its use has been mostly limited to external applications (e.g., on the skin) given the induced inflammatory and toxic responses. This derives from its reactivity towards functionalities on the tissue surface, the exothermic nature of the reaction and, more importantly, the release of formaldehyde and cyanoacetate during the degradation of the material.

U.S. Patent Application Publication No. 2011/0021965 describes biodegradable and biocompatible tissue adhesives based on a combination of nanotopography and mild surface chemistry. A layer of dextran-aldehyde glue is used to coat the nanotextured surface enabling adhesion in wet environments. WO 2012/030570 describes articles containing substantially cylindrical protrusions in combination with a surface treatment. The protrusions contain a stiff resin having a Young's modulus greater than 17 MPa. Both the '965 application and the '579 application describe performance by measuring the shear adhesion. However, the forces achieved were too low for most clinical applications.

There is a need for improved adhesive systems that exhibit 90° pull off adhesive strengths that are suitable for clinical applications. There is moreover a need for improved adhesive systems that allows for the use of tissue adhesives, the use of which in the clinic, absent the present system, is associated with adverse effects, such as for example inflammatory or toxic responses.

Therefore, it is an object of the invention to provide adhesive systems that exhibit 90° pull off adhesive strengths that are suitable for clinical applications and methods of making and using thereof.

Another object of the invention is to provide adhesive systems that exhibit 90° pull off adhesive strengths that are suitable for clinical applications while minimizing the toxicity issues/adverse side effects and/or adverse reactivity associated with tissues adhesives and methods of making and using thereof.

SUMMARY OF THE INVENTION

Adhesive articles containing microtopography, such as microprotrusions, and a coating of an adhesive glue are described herein. In some embodiments, the adhesive glue exhibits toxic and/or adverse side effects and/or tissue reactive functional groups that cause adverse effects. The microtopography allows for the use of less than an effective amount of the adhesive glue when used alone while providing 90° pull adhesive strengths necessary for clinical applications. The 90° pull adhesive strengths are comparable to or higher than the strengths observed for the adhesive glue alone without the microtopography. The reduction in the amount of adhesive required minimizes or prevents the toxicity and/or adverse side effects for adhesive glues that exhibit such effects.

The articles described herein contain a substrate. The substrate can contain or be formed of a biodegradable material, a non-degradable material, or combinations thereof. In some embodiments, the substrate is biodegradable in whole or in part. The articles described herein contain a plurality of microfeatures. In some embodiments, the microfeatures are microprotrusions. The protrusions can be any shape, such as cones, pillars, cylinders, frustum of a cone, prism having a polygonal cross section, regular or irregular pyramids, and combinations thereof. In some embodiments, the protrusions are not substantially cylindrical.

In some embodiments, the microstructures are cones, cone-shaped, or structures where the base is circular or semi-circular and has a diameter greater than the diameter of the tip. In some embodiments, the average height of the structures is greater than about 10 microns, such as from about 11 microns to about 20 microns, preferably from about 13 microns to about 20 microns, more preferably from about 15 to about 20 microns. In some embodiments, the average height is about 13 microns or about 19 microns. In some embodiments, the protrusions have the height described above and an average base width of from approximately 1 micron to approximately 10 microns, preferably from about 2 to about 8 microns, preferably from about 2 to about 7 microns, preferably from about 3 to about 7 microns, preferably about 3, 4, 5, 6, or 7 microns, more preferably about 5 microns. In some embodiments, the protrusions have the average height and base diameter described above and an aspect ratio (ratio of average protrusion height to average protrusion base diameter) of less than 7, 6, 5, 4, 3, or 2, such as about 4.

In some embodiments, the adhesive glue exhibits toxic and/or adverse side effects and/or contains reactive functional groups, the reaction of which causes adverse or toxic effects. For example, adhesives having highly reactive functional groups can form covalent bonds in a highly exothermic reaction. The heat generated can adversely affect the underlying tissue. Not all adhesives that contain reactive functional groups that react with tissue to form bonds are necessarily toxic. Toxicity can arise from the byproducts formed from degradation of the adhesive. For example, cyanoacrylate toxicity is due in large part to the formation of formaldehyde and cyanoacetate during in vivo degradation.

Exemplary adhesive glues include, but are not limited to, cyanoacrylates, such as methyl-2-cyanoacrylate, ethyl-2-cyanoacrylate, isobutyl-2-cyanoacrylate, octyl-2-cyanoacrylate, and butyl-2-cyanoacrylate; aldehyde adhesives, such as dextran-aldehyde, acrylate adhesives, urethane adhesives, hydroxysuccinimide adhesives, catechol-containing adhesives, such as DOPA adhesives, and combinations thereof. In some embodiments, the adhesive glue is in the form of a thin coating which does not significantly compromise the presence of the protrusions. For example, in some embodiments, the thickness of the coating is less than 75% of the average height of the microprotrusions.

The articles described herein exhibit a 90° pull off adhesion of at least about 1.0, 1.25, or 1.5 N/cm$^2$. The articles described herein can contain less adhesive than when the adhesive is used alone without microtopography and yet exhibit equivalent or improved adhesive strength with little or no toxicity and/or inflammation or other adverse side effects compared to a clinically effective amount of the adhesive alone. In some embodiments, the adhesive systems do not exhibit acute toxicity and/or inflammation (e.g., at the time of application or shortly thereafter) or chronic toxicity and/or inflammation (e.g., after an extended period of time after application).

BRIEF DESCRIPTION OF THE DRAWINGS

FIG. 1A are representative SEM images of four (4) different PDMS patterned surfaces patterned from the silicon mold obtained through chemical etching. All samples were tilted at a 30° angle. Scale bar represents 5 μm. B=base diameter, H=height, and P=pitch. FIG. 1B is a graph showing the relative increase in surface area for the different topographies when compared with a flat substrate. FIG. 1C is a schematic of the spin coating methodology to achieve thin CA coatings. FIG. 1D are representative SEM images of PDMS patterned surfaces after spin coating with cyanoacrylate (CA). All samples were tilted at a 30° angle. Scale bar represents 5 μm. FIG. 1E is a graph showing the pull-off adhesion forces for different surface topographies and coating procedures using PDMS as patch material. 5 μL of CA was selected for the spin coated condition to avoid an excess of glue that would slough off from the patch upon application to tissue. FIG. 1F are representative SEM images of PCL patterned surface (topography 4) before and after spin coating with CA. Scale bars represent 10 μm. FIG. 1G is a graph showing the pull-off adhesion forces for different surface topographies and coating procedures using PCL as patch material. The adhesion force for a flat PCL substrate without glue coating was approximately 0.3 N/cm$^2$.

FIG. 2 is a graph showing the adhesion force of CA-coated PCL surfaces against intestine tissue, measured after 1 hour of immersion in PBS. Patterned spin-coated samples demonstrated stronger adhesion than flat spin-coated samples and comparable to flat PCL samples coated with 5 μL of CA. Spin-coating reduces the amount of CA glue to values significantly lower than 5 μL of glue.

FIG. 3A is a table showing the contact angles of water and CA on flat and patterned PCL samples. Chemical mapping of IO nanoparticles encapsulated within CA demonstrated that CA covered the patterned area. Scale bar 10 μm. FIG. 3B is a graph showing the quantification of CA on flat and patterned spin-coated PCL patches through ICP-AES (n=5 per condition). The CA amounts on spin-coated flat substrates were 13±2 times less than 5 μL (non spin-coated) CA coated substrates. FIG. 3C is an SEM image of patterned PDMS after adhesion testing against ex vivo intestine tissue. Tissue residue (T) was visible on the patch surface and was interlocked with the surface topography (P). Scale bar 20 μm.

FIG. 4A are graphs showing fibrotic capsule thickness surrounding the patterned implant, the inflammatory infiltrate, and the density of CD68+ cells (0-negligible to 4-severe) 1 and 3 weeks after implantation; chronic inflammation was characterized (n=3 per formulation and time point) based on the fibrotic capsule thickness surrounding the patterned implant, the inflammatory infiltrate, and the density of CD68+ cells (0-negligible to 4-severe). FIG. 4B is a graph showing the adherence of CA spin-coated patterned and flat PCL patches to the colon, evaluated upon patch placement by a single surgeon blinded to patch topography (n=8 for flat samples, n=11 for patterned samples). FIG. 4C is a graph showing abdominal adhesions (0-10 for no to severe adhesions covering the abdominal space) 2 weeks post-repair with patterned spin-coated patch (n=3), graham patch (n=2), or without surgical repair (sham, n=2).

DETAILED DESCRIPTION OF THE INVENTION

I. Definitions

"Shear adhesion" or "shear adhesive strength" as used herein refer to the force required, under specified test conditions (surface area, weight load), to slide a standard area of an adhesive article from a standard flat surface in a direction parallel to the surface. The shear adhesion is not typically an accurate predictor of suitability for clinical applications since the exposure of the adhesive to tensile forces is limited, and the values recorded are highly dependent of the pre-load applied to the sample during testing. Also, differences in surface roughness of the substrate also affect the measured shear adhesive strength.

"90° pull off adhesion" as used herein refers to the adhesion value obtained by attaching an adhesive article or sample to wet tissue, such as the serosol side of porcine intestine tissue, immobilized on a flat substrate, such as a metallic stub. The 90° pull off adhesion test determines the greatest perpendicular force (in tension) that a surface area can bear before adhesive detachment.

"Toxicity", as used herein, means the ability of a material or device to elicit an undesirable local (e.g. tissue inflammation) or systemic effect upon implantation in or on a recipient. This undesirable effect may result from the interaction of the material or device, or their respective byproducts, with biological tissue and/or the surrounding environment during or after implantation or application.

"Tissue reactive functional group", as used herein, means functional groups that generate a tissue response after covalent or non-covalent bonds interaction with the underlying tissue. In some embodiments, the functional groups are highly reactive and result in adverse effects, for example, on the tissue during and/or after the reaction. Such adverse effects include, but are not limited to, the generation of heat (e.g., exothermic reaction) and/or the formation of byproducts that generate an inflammatory or toxic response.

"Microprotrusion", as used herein, refers to microscale features that extend from a surface. The features can have a variety of shapes including, but not limited to, cones, pillars, and cylinders.

As used herein, "biocompatible" refers to the ability of a structure or a material to perform its desired function in clinical setting, while eliciting little or no undesirable local or systemic effects to the recipient, but generating the most appropriate beneficial cellular or tissue response in that specific situation, and optimizing the clinically relevant performance of that therapy. (See Williams, Biomaterials 29 (2008) 2941-2953).

As used herein, the term "biodegradable" refers to substances that are degraded under physiological conditions. In some embodiments, a biodegradable substance is a substance that is broken down (e.g., when introduced into cells, in vivo) by the cellular machinery and/or by chemical processes (e.g., hydrolysis, enzyme mediated degradation, and/or oxidative mediated degradation) into components that can either be re-used and/or disposed of without significant toxic effect (e.g., on cells (e.g., fewer than about 20% of the cells are killed when the components are added to cells in vitro)). The components typically do not induce inflammation or other adverse effects in vivo. The components can be molecular species and/or fragments of the substance. In some embodiments, the chemical reactions relied upon to break down the biodegradable compounds are uncatalyzed. As examples, "biodegradable" polymers are polymers that degrade to other species (e.g., monomeric and/or oligomeric species) under physiological or endosomal or lysosomal conditions. The polymers and polymer biodegradation products can be biocompatible. Biodegradable polymers are not necessarily hydrolytically degradable and may require enzymatic action to fully degrade. Biodegradation mechanisms can include, for example, hydrolytic degradation, enzymatic degradation, and mechanisms in which the environment naturally introduces degradation factors, and/or where a catalyst is introduced to trigger degradation.

As used herein, the term "biological tissue" refers to a collection of similar cells combined to perform a specific function, and can include any extracellular matrix surrounding the cells.

The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, RNA, proteins, peptides, polysaccharides and any combinations of these components.

II. Adhesive Articles

Adhesive articles containing microtopography, such as microprotrusions, and a coating of adhesive glue, preferably an adhesive having known toxicity and/or tissue reactive functional groups are described herein. The articles described herein exhibit a 90° pull off adhesion of at least about 1.0, 1.25, or 1.5 N/cm$^2$. The articles described herein can contain less than the therapeutically effective amount of the adhesive when the adhesive is used alone without microtopography and yet exhibit equivalent or improved adhesive strength with little or no toxicity and/or adverse side effects.

A. Substrate

The articles described herein contain a substrate. The substrate can contain or be formed of a biodegradable material, a non-degradable material, or combinations thereof. In some embodiments, the substrate is biodegradable in whole or in part.

Suitable biodegradable materials include, but are not limited to, aliphatic polyesters, poly(amino acids), poly(etheresters), polyalkylene oxalates, poly(carbonates), poly(iminocarbonates), poly(ortho esters), poly(oxaesters), poly (amidoesters), poly(anhydrides), such as poly(glycerol sebacate) (PGS) and poly(glycerol sebacate acrylate) (PGSA), polyphosphazenes, poly(lactic-co-glycolic acid) (PLGA), polycaprolactone (PCL), polyglycolide (PGA), polylactic acid (PLA), poly-3-hydroxybutyrate (PHB), star-poly-caprolactone-co-D,L-lactide, poly(tri-methyl carbonate-co-caprolactone), poly(ethylene glycol) (PEG), polyurethanes, parylene-C, poly(citric-diol), hyaluronic acid, collagen, elastin, laminin, gelatin, chondroitin sulfate, dextran, chitosan, alginate, keratin, carbon nanotubes, agrose, or combinations thereof. In some embodiments, the material is polycaprolactone (PCL).

Suitable non-biodegradable materials include, but are not limited to, acrylics, butyl rubber, ethyl vinyl acetate, poly (amide imides), poly(etherketones), polycarbonates, polyolefins, such as polyethylenes and polypropylenes, polybutylene terephthalates, polydimethylsiloxane (PDMS), polyethylene terephthalates, polyamides, polyvinylidene fluoride, polyacrylates, such as polymethylmethacrylate and polyhydroxyethylmethacrylate, polyacrylamides, such as poly(N-isopropylacrylamide), and polyvinylalcohols.

In some embodiments, the material is hydrophobic. For example, flat, non-patterned PCL used in the examples has a water contact angle of 96±4°. The addition of the microfeatures increases the contact angle of the surface. In the case of the micropatterned PCL used in the examples, the water contact angle increased to 128±6°. For embodiments where the adhesive glue is considered hydrophobic, such as cyanoacrylate, the contact angle of the adhesive is reduced when measured on a patterned hydrophobic surface which results in better spreading of the adhesive on the surface. In some embodiments, the water contact angle of the micropatterned substrate is at least about 100, 105, 110, 115, 120, 125, or 130°.

B. Microfeatures

The articles described herein contain a plurality of microfeatures. In some embodiments, the microfeatures are microprotrusions. The protrusions can be any shape, such as cones, pillars, cylinders, frustum of a cone, prism having a polygonal cross section, regular or irregular pyramids, and combinations thereof. In some embodiments, the protrusions are not substantially cylindrical. In some embodiments, the protrusions are cone-shaped, where the base has a larger average diameter than the tip.

The protrusions can be incorporated into or onto a single site or plane of the article or multiples sites or planes of the article. The protrusions can also be layered, such that multiple layers of protrusions are found on one more site or planes of the article. Each layer of protrusions can have the same composition and/or dimensions and or different composition and/or dimensions.

The protrusions can be formed of the same material used to form the substrate or one or more different materials than the material used to form the substrate. As an example, the protrusions can include a material that is stiffer or harder than a composition included in the substrate. The stiffer composition can allow the protrusions to more easily penetrate an application site (e.g., tissue), thereby increasing contact area and adhesion. At the same time, the less stiff composition allows the substrate to be flexible and easily conformable to the application surface.

In some embodiments, the protrusions and the substrate can include compositions with different degradation rates, which can affect delivery of an active agent, if applicable. For example, one portion of an adhesive article can degrade quickly to provide a bolus delivery of an agent, and another portion of the adhesive article can biodegrade relatively slowly to provide an extended release of the agent. In certain embodiments, the protrusions have lower degradation rates than the substrate so the protrusions do not degrade quickly.

In some embodiments, the material used to prepare the protrusions is selected to have one or more desired mechanical properties, such as Young's modulus. In some embodiments, the Young's modulus is from about 1 MPa to greater than 100 MPa. In some embodiments, the material has limited elasticity, having a Young's modulus greater than 50, 60, 70, 80, 90, or 100 MPa. In other embodiments, the material is elastic having a Young's modulus is less than 17 MPa, such as less than 16, 15, 14, 13, 12, 11, 10, 9, 8, 7, 6, or 5 MPa.

In some embodiments, the substrate and/or the protrusions can be porous. Porosity can enhance in-growth of tissue into the adhesive article and improve securement of the article to the tissue (e.g., by acting as a mechanical interlock). Porosity can also be selected to control the biodegradation of the adhesive article and/or the delivery of an active agent. In some embodiments, the substrate and/or the protrusions have a porosity of greater than approximately 10%, 15%, 20% 25%, 30%, 40%, 50%, 60%, 70%, or 80%. The substrate and/or the protrusions can have an average pore size of from approximately 10 nm to approximately 1 micron.

The protrusions can have an average height from about 5 microns to about 50 microns, preferably from about 5 microns to about 40 microns, more preferably from about 5 microns to about 30 microns. In some embodiments, the average height is greater than about 10 microns, such as from about 11 microns to about 20 microns, preferably from about 13 microns to about 20 microns, more preferably from about 15 to about 20 microns. In some embodiments, the average height is about 13 microns or about 19 microns.

The protrusions can have an average base width of from approximately 1 micron to approximately 10 microns, preferably from about 2 microns to about 10 microns, more preferably from about 2 microns to about 8 microns, most preferably from about 3 microns to about 6 microns. In some embodiments, the average base width is about 5 microns. The protrusions can have an average tip width of from approximately 0.05 microns to approximately 10 microns.

The protrusions can have an average center-to-center pitch of from approximately 0.2 microns to approximately 500 microns, preferably from about 1 micron to about 250 microns, preferably from about 1 micron to about 100 microns, more preferably from about 1 micron to about 50 microns, most preferably from about 1 micron to about 25 microns. In some embodiments, the average center-to-center pitch is from about 5 microns to about 20 microns, preferably from about 5 microns to about 15 microns. In some embodiments, the pitch is about 10 microns.

The protrusions can have an average height to base width ratio of from approximately 0.1:1 to approximately 500:1, preferably 1:1 to about 250:1, preferably from 1:1 to about 100:1, more preferably from about 1:1 to about 50:1, most preferably from about 1:1 to about 25:1. In some embodiments, the ratio is from about 1:1 to about 20:1, preferably from about 1:1 to about 15:1, more preferably from about 1:1 to about 10:1. In particular embodiments, the ratio is from about 2:1 to about 7:1, such as about 3:1, 4:1, 5:1, or 6:1. In some embodiments, the ratio is about 4:1.

The density of the protrusions can be manipulated to vary the relative surface area of the pattern surface compared to a flat (e.g., non-patterned surface). In some embodiments, the introduction of the microfeatures increases the surface area by at least about 1.0, 1.25, 1.5, 1.75, 2.0, 2.25, 2.50, 2.75, or 3.0 or greater compared to a flat, non-patterned surface.

In particular embodiments, the microstructures are cones, cone-shaped, or structures where the base is circular or semi-circular and has a diameter greater than the diameter of the tip. The average height of the structures is greater than about 10 microns, such as is about 11 microns to about 20 microns, preferably from about 13 microns to about 20 microns, more preferably from about 15 to about 20 microns. In some embodiments, the average height is about 13 microns or about 19 microns. The protrusions can have an average base width of from approximately 1 micron to approximately 10 microns, preferably from about 2 to about 8 microns, preferably from about 2 to about 5 microns, preferably from about 3 to about 7 microns, preferably about 3, 4, 5, 6, or 7 microns. The protrusions have an aspect ratio (ratio of average protrusion height to average protrusion base diameter) of less than 7, 6, 5, 4, or 3.

C. Adhesive Glue

The substrate and/or microfeatures, in whole or in part, are coated with one or more adhesive glues. In some embodiments, the adhesive glue is a mixture of at least two adhesive glues or at least two different adhesive glues are coated on at least two different areas of the substrate and/or microfeatures. In some embodiments, the adhesive glue exhibits or causes toxic and/or adverse side effects when used in a therapeutically effective amount in the absence of the microfeatures. Not all adhesives that contain reactive functional groups that react with tissue to form covalent bonds are necessarily toxic. Toxicity can also arise from the byproducts formed from degradation of the adhesive. For example, cyanoacrylate toxicity is due in large part to the formation of formaldehyde during degradation. Adverse side effects can arise due to the presence of highly reactive functional groups that, for example, generate heat (e.g. exothermic reaction) upon reaction that can damage tissue.

Exemplary adhesives include, but are not limited to, cyanoacrylates, such as methyl-2-cyanoacrylate, ethyl-2-cyanoacrylate, isobutyl-2-cyanoacrylate, octyl-2-cyanoacrylate, and butyl-2-cyanoacrylate; aldehyde adhesives, such as dextran-aldehyde; acrylate adhesives; urethane adhesives; hydroxysuccinimide adhesives, catechol-containing adhesives (such as those described in U.S. Patent Application Publication No. 2005/0201974), such as DOPA adhesives, and combinations thereof.

The incorporation of microfeatures, such as microprotrusions, allows for application of a thin coat of adhesive, which is less than the amount of adhesive typically used in the absence of the microtopography, which exhibiting 90° pull off adhesive strengths necessary for clinical applications. In some embodiments, the thickness of the coating is such that it does not significantly compromise the presence of the protrusions. For example, the thickness of the coating is less than 75% of the height of the microprotrusions, such as less than 70, 65, 60, 55, 50, 45, 40, 35, 30, 25, 20, 15, 10, or 5%.

In some embodiments, the thickness of the coating is from about 1 micron to about 5 microns, preferably about 1 micron to about 4 microns, preferably about 2 microns to about 3 microns. In some embodiments, the coating thickness is about 2.5 microns. The thickness of the adhesive coating may be controlled by the spin coater speed.

The dimensions of the features on the articles described herein, particularly the height of the features, is substantially greater than the prior art features.

D. Sacrificial Layer

In some embodiments, the articles contain one or more sacrificial layers coated onto the adhesive layer to protect the adhesive layer prior to application. For example, cyanoacrylates can react with the moisture in the air prior to application. A protective layer can act as a barrier to prevent reaction with ambient moisture.

The one or more sacrificial layers can also allow the adhesive articles to be adjusted or re-positioned before the adhesive article completely adheres to its intended surface. The sacrificial layers can be removed from the surface of the substrate and/or the protrusions before the adhesive article is completely adhered to the application site. Chemical and/or physical interactions with tissue can be one mechanism through which the sacrificial layer(s) is removed from the surface of the adhesive article. For example, the sacrificial layer can include a salt coating or barrier that slowly dissolves when applied to tissue. The slow dissolution provides the user time to re-adjust or re-position adhesive article before the article adheres too strongly to the tissue. Other methods through which the sacrificial layer can be removed include, but are not limited to, light, pH, temperature, sound and/or physical mechanisms.

The adhesive article can include pressure-sensitive particles that contain a release agent (e.g., biomolecules). After the adhesive article is correctly positioned, sufficient pressure or another stimulus can be applied to release the release agent and/or achieve adhesion. Alternatively, the sacrificial layer can be applied to the application site prior to contacting the adhesive article to the site.

In other embodiments, the sacrificial layer is engineered to stay at an applied adhesion site and to degrade over a desired period of time after the adhesive article is removed from the adhesion site. For example, patterns resulting from contact of the adhesive article containing the sacrificial layer can remain on the contacting tissue surface after the article is removed. These patterns can, for example, provide sites for cell attachment or localized points of adhesion and/or visible marks for surgical applications.

Exemplary materials include, but are not limited to, materials that dissolved, preferably rapidly, in an aqueous environment, such as sugars, or polymers including polyethyleneglycol, polyvinylalcohol, or polyacrylic acid. In other embodiments, the sacrificial layer material has pH dependent solubility, such as acrylic polymers (e.g., Eudragits), celluloses or chitosan and derivatives thereof. Other polymers include biodegradable polymers including, but not limited to, PLA, PGA, PLGA, as we as the polymers listed above. The sacrificial layer may also be a release liner, such as crosslinkable silicone, that is removed by physical means from the surface.

E. Therapeutic, Prophylactic, and/or Diagnostic Agents

The substrate and/or the microfeatures can include one or more therapeutic agents, prophylactic agents, diagnostic agents, and/or nutraceuticals. The agents can be a small molecule (e.g., molecular weight less than 2000, 1500, 1000, 750, or 500 atomic mass units (amu)) or a biomolecule, such as peptides, proteins, enzymes, nucleic acids, polysaccharides, and combinations thereof.

Exemplary class of agents include, but are not limited to, anti-viral agents (e.g., anti-AIDS agents), chemotherapeutics (e.g., anti-cancer agents), antibiotics, immunosuppressants, enzyme inhibitors, neurotoxins, opioids, hypnotics, anti-histamines, lubricants, tranquilizers, anti-convulsants, muscle relaxants, anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and pro- or anti-adhesion molecules, vasodilating agents, inhibitors of DNA, RNA or protein synthesis, anti-hypertensives, analgesics, anti-pyretics, steroidal and non-steroidal anti-inflammatory agents, pro- or anti-angiogenic factors, pro- or anti-secretory factors, anticoagulants and/or anti-thrombotic agents, local anesthetics, ophthalmics, prostaglandins, anti-depressants, anti-psychotic substances, anti-emetics, growth factors, proton pump inhibitors, hormones, vitamins, gene delivery systems, and imaging agents.

Examples of biomolecules include, but are not limited to, growth factors or ligands such as, transforming growth factor beta (TGF-β), acidic fibroblast growth factor, basic fibroblast growth factor, epidermal growth factor, insulin growth factor I and II (IGF-I and II), vascular endothelial-derived growth factor, bone morphogenetic proteins, platelet-derived growth factor, heparin-binding growth factor, hematopoetic growth factor, and peptide growth factor. Extracellular matrix components, e.g., collagen, fibronectin, laminin, elastin, etc., can also be combined with the substrate, protrusions, and/or the adhesive glue to manipulate cell recruitment, migration, and metabolism, and the degradation and mechanical properties of the material. In some embodiments, proteoglycans and glycosaminoglycans are covalently or non-covalently attached to the substrate, protrusions, and adhesive glue.

E. Cells

In some embodiments, the article or a portion of there is seeded with cells or contains cells. Exemplary cell types include, but are not limited to, kerotinocytes, fibroblasts, ligament cells, endothelial cells, lung cells, epithelial cells, smooth muscle cells, cardiac muscle cells, skeletal muscle cells, islet cells, nerve cells, hepatocytes, kidney cells, bladder cells, urothelial cells, stem or progenitor cells, neurobalstoma, chondrocytes, skin cells and bone-forming cells.

III. Methods of Making

The adhesive articles described herein can be fabricated with a variety of techniques. Exemplary techniques include contact lithography, nanodrawing, photolithography followed by etching or nanomolding, and nanocasting using vertically aligned multi-walled carbon nanotubes. See, e.g., Geim A K, Dubonos S V, Grigorieva I V, Novoselov K S, Zhukov A A, Shapoval S Y. Microfabricated adhesive mimicking gecko foot-hair. Nat Mater 2003; 2(7):461-3; eong H E, Lee S H, Kim P, Suh K Y. Stretched Polymer Nanohairs by Nanodrawing. Nano Letters 2006; 6(7):1508-1513; and Yurdumakan B, Raravikar N R, Ajayan P M, Dhinojwala A. Synthetic gecko foot-hairs from multiwalled carbon nanotubes. Chem. Commun. (Camb) 2005(30):3799-801. In various embodiments, fabrication methods avoid high temperatures and/or harsh chemical modifications.

In some embodiments, a template is prepared using, for example, a combination of photolithography followed by reactive ion etching (RIE). The template includes a plurality of mold cavities having the shape(s), patterning(s) and dimensions of protrusions, or shapes that give rise to the protrusions. In other embodiments, a mold with protrusions is transferred to a second mold, generating the equivalent cavities (e.g., this process can be done by soft lithography). The substrate material is then deposited in this second mold. The material(s) for the protrusions and/or the substrate is filled into cavities and placed on the template. In some embodiments, no high vacuums are used to fill the cavities, but in other embodiments, vacuums and/or temperature variations are used to fill the cavities. The material(s) for the protrusions and the substrate is cured, for example, using heat ultraviolet radiation in minutes at room temperature. In other embodiments, the material(s) for the protrusions is molten at high temperatures to fill the cavities on the template, followed by cooling to achieve the solid state. The cured material is then separated from the template to provide an uncoated adhesive article.

To fabricate complex structures, the template can have a photoresist patterned on top to form larger mold cavities. Multiple layers of photoresists can be patterned using spin-on and laminated resists for larger structures. To release the structures, the photoresists can be dissolved in a solvent.

The adhesive glue can be applied to the microprotrusions and/or substrate using techniques known in the art. Methods of coating include, but are not limited to, spin-coating, solvent-casting, Langmuir-Blodgett deposition, and chemical vapor deposition (CVD).

In embodiments where the article contains one or more therapeutic, prophylactic, and/or diagnostic agents and/or cells can be incorporated similarly to the adhesive glue. Certain materials, for example, agents and/or cells, can also be intimately mixed with the materials used to form the substrate and/or the protrusions.

In some embodiments, the molds for forming the microtopography were prepared using photolithography. For example, a substrate, such as a silicon wafer with an oxide layer having a desired thickness (e.g., 2 microns) was baked to dehydrate the surface and spin coated with a material to promote resist adhesion. Suitable materials for promoting resist adhesion include, but are not limited to, hexamethyldisilazane (HMDS). The coated substrate can be baked to yield a resist film of the desired thickness. The resist exposure can be done using techniques/apparatus known in the art, such as a Karl Suss MA-6 contact aligner. The exposure dose and development time can be readily determined by one of ordinary skill in the art. The PR micro-patterned silicon wafer can be treated with an oxygen plasma.

Micropatterns can be transferred from the photoresist to the underlying oxide layer by techniques known in the art, such as reactive ion etching, to generate the final micro-mold. For example, a Multiplex Reactive Ion Etcher (Surface Technology Systems) was used to etch an oxide layer in $CHF_3/CF_4$ at gas flow rates of 14.4 and 1.6 sccm, respectively, at a pressure of 20 mTorr and RF power level of 200 W, resulting in an oxide etch rate of approximately 3 nm/second. After the etching, the PR layer was removed by immersing the substrate into acetone and SVC-12 (Microchem) for 30 min each, and EKC-270 stripper for up to 3 h. The substrate was then washed with DI water thoroughly for 10 min, and spin-dried.

Patterning of the article can be done using techniques known in the art. For example, to pattern film, patches, etc., a negative mold can be prepared using an appropriate material, such as acrylated polyurethane resin (PUA) through soft-lithography using the positive silicon mold, followed by surface treatment with an appropriate material, such as (tridecafluoro-1,1,2,2-tetrahydrooctly)trichlorosilane (TTT, Gelest).

In some embodiments, PDMS pre-polymer was poured onto the PUA mold, degassed under vacuum and cured overnight at 60° C. For PCL micropatterning, negative PDMS molds were fabricated directly from the silicon molds, followed by surface treatment with TTT. For embodiments, containing polycaprolactone (PCL), PCL (e.g., Mw=43,000-50,000 g/mol, Polysciences) films were melted at 130° C. on top of negative PDMS molds followed by compression against a Teflon plate to assure pattern transfer. PCL films were carefully removed after cooling. The efficiency of pattern transfer was evaluated through scanning electron microscopy (SEM, FEI/Phillips XL30 FEG-ESEM). In some embodiments, the adhesive glue can be applied by spin coating onto the patterned surface. CA coating thickness can be determined through the analysis of SEM images obtained from cross-sections of coated and uncoated patterned surfaces (n=4 different substrates per experimental condition). The differences in height between non-coated and CA spin-coated patterns can be used to determine the CA glue layer thickness.

IV. Methods of Using

The adhesive articles described herein can be used in any application where adhesiveness is required or desired. The surface(s) to which the articles are applied can be dry or wet (e.g., in an aqueous environment, such as biological tissue). The adhesive articles described herein can be used in the body or on the body (e.g., on the skin). The articles described herein can be used in a variety of applications, including, but not limited to, wound or surgical site closure or sealing, tissue affixation (e.g., in addition to or as a replacement for sutures and staples), bioactive agent delivery vehicles (e.g., delivery of antibiotics, drugs, etc.), waterproof sealants for hollow organ anastomoses, medical devices for fixation, skin adhesion, physico-chemical barrier to prevent tissue infection, physical support for tissue re-enforcement, mesh grafts to treat hernias, ulcers, and burns, hemostatic wound dressings, patches for diabetic ulcers, abdominal implants to prevent adhesions, biodegradable adhesive, in vivo and in vitro sensors, catheters, surgical glue, cardiac patches/glues, bile-duct patches/glues, intestinal stents, coatings for metals, microfabrication applications. The adhesive articles can adapt to, or recover from various mechanical deformations while remaining strongly attached to the underlying tissue.

In some embodiments, the articles described herein are used in medical applications (e.g., as medical devices). More specifically, adhesive articles can be used to join tissue (e.g., one or more tissue in vivo). Conformal sealing of damaged tissue can be challenging due to the requirement of good surface adhesion as well as shear strength during tension loading. For example, lung punctures, punctured blood vessels and anastomosis of the intestine can be challenging wounds to seal. The adhesive articles described herein can be designed to match tissue mechanical properties to provide conformal wound closure and sealing. Such adhesive articles can be particularly useful in applications where there is considerable tissue movement. As the adhesive articles described herein are applied to tissue, the tissue can conform to the surfaces of the protrusions and/or the substrate, thereby increasing contact area and adhesion between the adhesive article and the tissue. In some embodiments, the protrusions penetrate into tissue to anchor the adhesive article to the tissue. But regardless of whether protrusions actually penetrate tissue or not, the protrusions, the substrate, and the tissue mechanically interface and engage to provide a mechanical interlock that resists shearing and pulling between adhesive article and the tissue.

As another example, the adhesive articles described herein can be used as surgical tape. A biocompatible, biodegradable surgical tape can be used, e.g., to stop bleeding during surgery but does not need to be removed before the surgeon sutures the wound closed. The tape may biodegrade over time.

In some embodiments, the adhesive article can be fabricated into a biodegradable stent. The stent can increase the diameter of a blood vessel to increase flow through the vessel, but since the stent is biodegradable, the blood vessel can increase in diameter with a reduced risk of thrombosis or covering the stent with scar tissue, which can re-narrow the blood vessel. The time a stent remains in place and retains its shape before degradation can vary from patient to patient and depend partially on the amount of blockage and the age of the patient (e.g., older patients may need more time to heal). In certain embodiments, the adhesive articles can cover an outer surface of a stent (with protrusions extending outward) to help adhere the stent to a vessel wall in a manner that is less damaging to the tissue than an uncovered stent. Similarly, the adhesive article can cover the surface of devices which are in contact with tissue to provide a suitable interface that can be adhesive to tissue.

Other applications include, but are not limited to, preventing air leaks following a lung resection; to reduce the time for surgical procedures (e.g., sutures may require aligning tissue with each stitch, but an adhesive tape may be able to align the tissue once); to seal dura; to ease laproscopic procedures (e.g., it can be difficult to tie knots in small spaces, but a tape can be rolled up and placed through a large bore needle or trocar, and unfolded on the surgical site); as a degradable skin adhesive (e.g., that can release agents as it degrades); as a hernia matrix to prevent or to reduce the need for stables or tacks; to prevent blood loss; to manipulate organs or tissues during surgical procedures (e.g., to push the liver aside and hold it in place); to secure corneal transplants in place; to patch a heart to deliver drugs and/or to reduce growth of the heart after myocardial infarction; to attach another material to a tissue (e.g., to enhance engraftment of graft tissue, or to bond a drug delivery device or scaffold or other construct to a tissue or organ); to augment sutures or staples; to distribute forces across tissue; to prevent leaks; as a barrier membrane on the skin to prevent evaporation of water from burnt skin; as a patch for delivery of anti-scar medication; to attached devices (e.g., drug delivery devices, sensors) to tissue; to attach devices (e.g., a drug delivery device) to mucus membrane (e.g., mouth, gut, anus, nostrils, vagina, etc.); to prevent adhesion of brain tissue to the skull after brain surgery or implantation of devices; as adhesive barriers (as applies to surgical applications) for tissue-tissue adhesion and/or tissue-device adhesion; to prevent blood loss from blood vessels; as a tape to secure devices within an oral cavity, such as to hold dentures and oral appliances; as a tape to anchor soft tissue to bone; to prevent peritoneal adhesion (e.g., where one side is adhesive and other is not), and/or to seal or treat patent foramen.

The adhesive articles described herein can also be used to coat tools, such as surgical instruments (e.g., forceps, retractors) or to enhance the ability of the tools to manipulate (e.g., grip) objects (e.g., tissue). The adhesive articles described herein can also be used in industrial applications where it is useful to have a degradable adhesive that is biocompatible (e.g., to reduce potential toxicity of the degradation products, such as marine applications (e.g., underwater use, attach to surface of boats, etc.). Other applications include to affix clothing to the skin, e.g., strapless bras, affixing electronics to substrates, such as tissue (e.g., skin) or clothing.

In embodiments in which the adhesive article a therapeutic, prophylactic, and/or diagnostic agent, the agent can be locally delivered where the adhesive article is placed. Because the adhesive article is generally elastic, it can conform to the application site and move with the patient as he/she moves.

A. Adhesive Strength

The articles described herein exhibit 90° pull off adhesive strengths suitable for clinical applications. In some embodiments, the 90° pull off adhesive strength is at least about 1.0, 1.25, 1.5, 1.75, 2.0, 2.25, 2.50, 2.75, 3.0, 3.25, 3.5, 3.75, or 4.0 N/cm$^2$ or greater. The data shows that the combination of microfeature shape, dimensions, and coating thickness of the adhesive glue allows one to maximize adhesive strength, particularly on wet tissue, while minimizing toxicity and tissue reactivity of the adhesive glue.

For example, four different topographies were prepared as shown in FIG. 1A: (1) cones having a base diameter of 4.4 microns, a height of 20.0 microns, and a pitch of 19.0 microns; (2) cones having a base diameter of 2.9 microns, a height of 20.3 microns, and a pitch of 10.0 microns; (3) cones having a base diameter of 2.6 microns, a height of 7.1 microns, and a pitch of 5.0 microns; and (4) cones having a base diameter of 4.9 microns, a height of 19.0 microns, and a pitch of 9.5 microns. Adhesive glue was then spin coated onto the patterned surfaces.

Patches with topography 4 had the highest adhesion forces. Although the total surface area of topography 4 was similar to topography 3 prior to spin-coating, the adhesion values of the two topographies were significantly different; the micropattern of topography 3 was easily occluded upon spin-coating because the feature height of topography 3 was lower than that of topography 4. CA coating of the highest aspect ratio pillars (topography 2) induced pattern collapse with no adhesion improvement. Increasing the density of similar sized features significantly enhanced the adhesion (see topography 1 vs. topography 4).). The density of pillars on the surface, and therefore the increase in contact area, had a major effect in enhancing adhesion. The patterned surfaces were able to retain more adhesive glue than the flat one after the spin coating procedure ($p<0.05$). However, given the increase in contact area, the amount of adhesive glue on the patterned samples per unit area was ~0.78 times that of the flat substrate. In other words, the adhesive glue layer was thinner on the patterned surface compared to the flat surface.

In vitro pull-off adhesion tests against wet intestine tissue confirmed the efficacy of topography in enhancing the adhesion force of thin adhesive glue coatings when comparing with a flat substrate. The adhesion force of spin coated adhesive glue on patterned surface was similar to the ones obtained for flat or patterned PCL coated with 5 μL of adhesive glue. The improved performance of the patterned samples was still visible if the samples were immersed in PBS over 1 hour. Importantly, this approach seems universal when using materials with different mechanical properties (i.e. stiffness), as it was demonstrated using both stiff PCL and elastic PDMS.

The inflammatory reaction to patterned spin coated samples was similar to that of patterned uncoated material at the early 1 week time point. At 3 weeks post implantation, the inflammatory reaction to the spin coated material slightly increased, as evidenced by higher incidence of vascularization and appearance of giant cells, while inflammation to uncoated material stabilized. Cell necrosis could be observed at 1 week for both conditions where adhesive glue was applied (spin coated or 5 μL); however after 3 weeks only the condition where 5 μL of CA was applied still induced necrosis. Initial cell necrosis may be justified by the reactivity of the adhesive glue towards the tissue surface, while long-term response by the release of toxic products. Implantation of samples coated with 5 μL of adhesive glue also resulted in more severe inflammatory response and thicker fibrotic capsule, compared to both patterned uncoated and spin coated samples at both time points, while no statistical differences in the inflammatory degree or fibrotic capsule thickness were observed between patterned uncoated and spin coated samples.

EXAMPLES

Example 1

Preparation of Patterned, Coated Surfaces

Silicon Micromolds Fabrication

Silicon wafers with an oxide layer were baked at 110° C. to dehydrate their surface and spin coated with hexamethyldisilazane at 5000 rpm for 10 seconds to promote resist adhesion. Photoresist (Shipley 1805) was then spin-coated (EVG101) on the wafers at 3500 rpm for 20 seconds. The wafer was softbaked on a hotplate at 115° C. for 1 minute to yield a resist film thickness of approximately 500 nm. Resist exposure was done with a Karl Suss MA-6 contact aligner with an exposure dose of 96 mJ/cm$^2$, and the resist was developed for 45 seconds in Shipley MF-319 developer followed by a 3-minute rinse in deionized (DI) water and spin drying. The etched wafer obtained had a positive configuration.

Micropatterning and Characterization of Polydimethylsiloxane (PDMS) and Polycaprolactone (PCL) Films For polydimethylsiloxane (PDMS) patterning, a negative mold was initially prepared with acrylated polyurethane resin (PUA) through soft-lithography using the positive silicon mold, followed by surface treatment with (tridecafluoro-1,1,2,2-tetrahydrooctly)trichlorosilane (TTT, Gelest). PDMS pre-polymer was poured onto the PUA mold, degassed under vacuum and cured overnight at 60° C.

For polycaprolactone (PCL) micropatterning, negative PDMS molds were fabricated directly from the silicon molds, followed by surface treatment with TTT. PCL (Mw=43,000-50,000 g/mol, Polysciences) films were melted at 130° C. on top of negative PDMS molds followed by compression against a Teflon plate to assure pattern transfer. After cooling, the PCL films were carefully removed. The efficiency of pattern transfer was evaluated through scanning electron microscopy (SEM, FEI/Phillips XL30 FEG-ESEM)

CA Spin Coating Procedure of PDMS and PCL Film

15 μL of CA (Dermabond®, Medstarsutures) was spin coated at 3000 RPM on PDMS and PCL patterned and flat surfaces. CA coating thickness was determined through the analysis of SEM images obtained from coated and uncoated patterned surfaces.

Pull-Off Adhesion Testing

Pull-off adhesion tests were performed using an ADMET eXpert 7601 universal tester, equipped with a 50N load cell. Experimental conditions included: (1) micropatterned surfaces spin coated with CA at 3000 RPM, (2) flat surfaces spin coated with CA at 3000 RPM, (3) flat surface with 5 μL of CA, or (4) patterned surface with 5 μL of CA (n=3 per condition for PDMS substrates, n=6 per condition for PCL substrates). 5 μl of glue was applied to non-spin coated substrates (as additional amounts of glue were easily displaced after application to tissue). To ensure uniform coating across the surface of spin coated patches, 15 μl of glue was applied. Immediately after CA coating, the samples were attached to the wet serosal side of porcine intestine tissue, previously immobilized in a flat metallic stub. Samples were cured for 5 min by exposure to air or for 1 hour immersed in phosphate buffer saline, followed by pull off at 8 mm/min. Adhesion force was recorded as the maximum force observed during pull off testing. The contact area between tissue and adhesive was circular with a diameter of 6 mm.

Characterization of CA-Coated PCL Surfaces

Contact Angle Analysis

The spreading of CA on flat and micropatterned PCL was evaluated through advancing contact angles measurement and compared with ultrapure water (n=4 per condition).

Chemical Mapping of CA Glue Layer

Energy-dispersive X-ray spectroscopy (EDX) was applied to visualize how CA covers the micropatterned surface. CA glue was mixed with iron oxide nanoparticles (IO, 10 nm, Oceananotech) functionalized with oleic acid for uniform dispersion, followed by spin coating at 3000 RPM for 3 min on a patterned PCL surface. The encapsulation of IO does not interfere with the glue layer thickness, as confirmed through SEM analysis. Data was collected at 25 kV using a X-ray detector coupled with FEI/Phillips XL30 FEG-ESEM. The iron signal could be easily detected and mapped through EDX.

CA Quantification

Quantification of CA in flat versus patterned samples after spin coating was performed through induced coupled plasma atomic emission spectroscopy (ICP-AES, ACTIVA-S Horiba Jobin Yvon). Patterned or flat patches spin coated with CA-IO glue, or CA-IO glue only were solubilized in acetone. IO particles were isolated from the organic materials through sequential centrifugations and re-suspended in chloroform. Following chloroform evaporation, the IO nanoparticles were digested in aqua regia, which was after evaporated, and re-suspended in aqueous 2% nitric acid. The relative amount of iron per sample was then evaluated and correlated to the amount of CA per sample (n=5 per condition).

Subcutaneous (s.c.) In Vivo Biocompatibility Studies of Micropatterned PCL

All surgical procedures were approved by the Institutional Animal Care and Use Committee (IACUC) of the Massachusetts General Hospital and performed according to the NIH Guidelines for the Care and Use of Laboratory Animals.

The biocompatibility profile was evaluated for patterned PCL, patterned PCL spin-coated with CA, patterned PCL covered with 15 μL of CA (n=3 per formulation and time point). PCL disks, with a diameter of 7 mm, were disinfected by UV exposure overnight. Adult female Lewis rats (Charles River Laboratories, Wilmington, Mass.) were used in this study. Six s.c. 1.5 cm long midline incisions were made on the back of each anesthetized animal. The patch coating procedure was performed in the operating room and the samples immediately and randomly implanted in the s.c. pockets. Animals were sacrificed at 7 and 21 days, and the implants and surrounding tissue harvested. Hematoxylin and eosin (H&E) and anti-CD68 stains were performed to characterize the inflammatory response.

In Vivo Functional Studies

All surgical procedures were approved by the Institutional Animal Care and Use Committee (IACUC) of the Massachusetts General Hospital and performed according to the NIH Guidelines for the Care and Use of Laboratory Animals. The use of flat and patterned CA spin coated PCL patches to close defects requiring surgical repair was evaluated in colon and stomach perforations using a rat model. Adult female Lewis rats (Charles River Laboratories, Wilmington, Mass.) were used. All PCL patches tested were disinfected by UV exposure overnight. For both models, a defect was created using a 3 mm diameter dermal biopsy puncher. Bleeding was controlled through compression and electro cauterization. For colon repair, flat or patterned patches with 7-8 mm in diameter were coated with a thin layer of CA and immediately applied to the defect. The degree of attachment was qualitatively evaluated by a blinded surgeon (n=8 for flat samples, n=11 for patterned samples).

Animals whose colon defect was closed with a patterned spin coated patch were survived for 7 days (n=6). H&E stain was used to evaluate the tissue response to the spin coated patterned patch. For stomach repair, experimental groups included: (1) 7 mm diameter patterned spin coated PCL patch, (2) Graham patch, or (3) sham operated animals where the defect was not closed. Defect closure using Graham patch consists in suturing the omentum over the defect to. A suture was used in this procedure. Animals were sacrificed at day 7 (n=3 for patterned spin coated patch, n=1 for Graham patch)

and day 14 (n=3 for patterned spin coated patch, n=2 for Graham patch, n=2 for sham animals) after the initial procedure. The degree of abdominal adhesions for each condition was evaluated and ranked from 0 (no adhesions) to 10 (extensive adhesions covering all abdominal cavity). H&E stain was used to evaluate tissue response to the different closure techniques.

Statistics Data are expressed as means±standard deviation. One-way ANOVA with post hoc Tukey was use to examine statistical difference in the experiments focused on: (1) determining the effect of topography and CA amount in the adhesive strength of PDMS and PCL patch materials, (2) evaluating the s.c. biocompatibility of non-coated and coated PCL patches, and (3) determining the degree of abdominal adhesion after stomach defect closure using different techniques. Unpaired t-test was used to compare the amount of CA glue retained in flat or patterned PCL surfaces after spin coating. Data were assumed to be significant when a P-value of 0.05 or less was obtained.

Results

Different micron-scale topographies were prepared through chemical etching of a silicon wafer, which was then used to pattern different materials such as PDMS (FIG. 1A). This size scale was selected to allow coating of a micron-scale layer of CA without compromising the presence of surface topography. The designs of the pillar arrays were chosen to evaluate the effect of surface contact area on adhesion strength of thin CA films (FIG. 1B), with up to a maximum of 2.6 fold increase for topography. Geometric correlations between the different topographies also allow comparing the effect of pillar aspect ratio and base diameter (topography 2 vs 4), pitch distance (topography 1 vs 4), and overall pattern scale (topography 3) on adhesion strength.

An initial screen to determine the effect of pillar arrays in enhancing adhesion was performed using elastic PDMS as substrate material. PDMS is a model material extensively used to test the effect of topography in adhesion since it can be easily and reproducibly patterned and it has good elastic properties. In vitro pull-off adhesion measurements were performed for coated surfaces 5 minutes after patch application to wet intestine tissue. This curing time was selected considering the average time spent during regular surgical application. The spin coating method employed (FIG. 1C) allowed obtaining a uniform layer of CA glue on the patterned surfaces (FIG. 1D). A significant increase in adhesion strength was observed for topography 4 ($p<0.05$), while only minor or no increase was observed for other topographies (FIG. 1E). Interestingly, topography 4 presents similar total surface area to topography 3 but the adhesion values observed were different, emphasizing the importance of pillar height in enhancing adhesion. Smaller pillar height (topography 3) results in almost complete pattern coverage with CA and in adhesion values similar to the flat surface. However, for the highest aspect ratio pillars tested (topography 2) CA coating caused pattern collapse with no improvement over adhesion. For the same pillar size (topography 1 vs topography 4), the density of pillars on the surface, and therefore the increase in contact area, had a major effect in enhancing adhesion.

Considering the screening results, topography 4 was selected for further studies. To allow translation for medical applications, a biodegradable and biocompatible material, polycaprolactone (PCL) was used as patch material. PCL is FDA-approved for internal application (e.g. biodegradable sutures) and different studies have demonstrated its favorable biocompatibility profile in wound closure applications. Given its low melting temperature (~60° C.), PCL can be easily patterned through hot embossing without requiring the use of organic solvents, and with high reproducibility over large surface areas.

The patterns obtained through this method, had an approximate height of 13.2±1.0 μm and base diameter of 5.15±0.4 μm. CA uniformly coated patterned PCL surfaces (FIG. 1F). From SEM measurements, the coating thickness at the base was approximately 2.6±1.4 μm.

In vitro pull-off adhesion tests against wet intestine tissue confirmed the efficacy of topography in enhancing the adhesion force of thin CA coatings when comparing with a flat substrate (FIG. 1G). The adhesion force of spin coated CA on patterned surface, was similar to the ones obtained for flat or patterned PCL coated with 5 μL of CA. The improved performance of the patterned samples was still visible if the samples were immersed in PBS over 1 hour (FIG. 2). Importantly, this approach seems universal when using materials with different mechanical properties (i.e. stiffness), as we have here demonstrated using both stiff PCL and elastic PDMS.

The hydrophobic nature of PCL is further enhanced in the presence of surface patterns, resulting in the increase of water contact angle from 96±4° (flat surface) to 128±6° (patterned surface). Given the hydrophobic nature of CA, its contact angle is reduced when measured on a patterned PCL surface (12±4°), when compared to a flat one (28±7°) (FIG. 2A). This results in better spreading of CA in the patterned versus the flat surfaces.

Chemical mapping was employed to evaluate how CA covers the pillar structures after spin coating. Given the similar chemical composition between CA and PCL, an indirect method, based on the detection of IO encapsulated within CA, was used. The presence of IO in CA does not interfere with the spin coating process and with the thickness of the final glue layer (FIGS. 1G and 3B). EDX analysis confirmed that CA glue covers the full pattern length, and therefore the area coated with CA is equivalent to the total surface area of the patterned patch. However, from SEM images more glue accumulation seems to occur at the base of the patterns (FIG. 1G).

The relative amount of CA glue for spin coated patterned surface, flat surface, or 5 μL of glue was quantified through ICP-AES based on the iron signal detected for encapsulated IO in CA glue. The spin coating process is able to reduce the amount of CA by 13±2 times on a flat substrate compared to 5 μL of glue applied without spin coating (FIG. 3C). The patterned surface was able to retain more CA than the flat one after the spin coating procedure ($p<0.05$). However, given the increase in contact area, the amount of CA on the patterned samples per unit area was ~0.78 times that of the flat substrate. In other words, the CA layer was thinner on the patterned surface compared to the flat surface.

To determine how tissue interacts with the surface topography, SEM images of patterned PDMS spin coated with CA were evaluated following pull off tensile testing from intestine tissue. These revealed interlocking of tissue with the surface topography (FIG. 3D). These data suggest that mechanical interlocking and increased contact area may mediate the enhanced performance of the patterned surfaces. This is further supported by the similar orders of magnitude in the increase in surface area (~2.3 times, for PCL patch material) and the increase in adhesion strength (~2.6 times, FIG. 1H), when comparing patterned and flat spin coated samples.

To evaluate how the amount of CA glue at the interface with tissue affects the tissue response, in vivo biocompatibility experiments were performed. H&E and anti-CD 68 stains were used to evaluate tissue response at 1 and 3 weeks after subcutaneous implantation. The inflammatory reaction to patterned spin coated samples was similar to that of patterned uncoated material at the early 1 week time point. At 3 weeks post implantation, the inflammatory reaction to the spin coated material slightly increased, as evidenced by higher incidence of vascularization and appearance of giant cells, while inflammation to uncoated material stabilized. Cell necrosis could be observed at 1 week for both conditions where CA was applied (spin coated or 5 µL); however after 3 weeks only the condition where 5 µL of CA was applied still induced necrosis. Initial cell necrosis may be justified by the reactivity of CA towards the tissue surface, while long-term response by the release of toxic products. Implantation of samples coated with 5 µL of CA also resulted in more severe inflammatory response and thicker fibrotic capsule, compared to both patterned uncoated and spin coated samples at both time points, while no statistical differences in the inflammatory degree or fibrotic capsule thickness were observed between patterned uncoated and spin coated samples (FIG. 4A). The histotoxicity of CA was highly dependent on the amount of glue applied to the tissue interface. Spin coating the glue reduced the amount of glue and its toxic products released during degradation, while increasing the interface surface area via microtopography maximizes tissue adhesion.

The ability of spin coated samples to promote functional closure of internal tissue defects was evaluated using rat models with colon or stomach puncture. The initial degree of adhesion of flat or patterned spin coated patches to the colon surface was classified by a blinded surgeon immediately after application to tissue. The adhesive patch was applied on top of the defect and statistically significant differences in the degree adhesion were found, confirming better performance of patterned over flat spin coated samples (FIG. 4B). Upon successful attachment, all patches resisted the peristaltic motions and remained covering the defect during the 7 days of the study. No major inflammatory response was observed surrounding the defect, confirming the favorable biocompatibility profile when a reduced amount of CA was used.

Patterned spin coated patches could also adhere to the stomach surface covering a puncture defect with a diameter of 3 mm and remain adherent for at least 14 days. As control, the stomach defect was closed using a Graham patch technique, routinely used for gastrointestinal defects. This involves suturing the omentum, known to contain progenitor cells that promote tissue repair, over the defect. Importantly, after 14 days of implantation minimal abdominal adhesions where observed for the animals whose stomach defect was closed with the pattern spin coated patch, while minimal-moderate or severe adhesions were observed from Graham patch and sham operated animals, respectively (FIG. 4C). These data suggests that the patch is able to provide a leak-proof seal of the defect. The impact of the CA glue in mucosa regeneration was evaluated through H&E staining of the tissue underlying the patch. Previous studies have demonstrated that exacerbated inflammatory response inhibit tissue repair and regeneration. By day 7 the defect was still visible for both Graham patch and patterned spin coated patch.

Surface topography, by increasing the contact area between substrate and tissue, enhances the performance of thin adhesive coatings. Importantly, it allows reduction on the amount of glue at the interface tissue-patch material, improving the biocompatibility profile of reactive glues without compromising its adhesive strength. This is believed to be the first demonstration correlating the amount of CA glue applied to tissue with the histotoxic and inflammatory responses observed. Based on this concept, other glue delivery approaches may be developed to maximize the adhesive strength of CA, while minimizing the toxicity induced. These approaches may expand the applicability and translation of CA glues beyond external application.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An adhesive article comprising a substrate comprising a surface, wherein the substrate surface comprises microprotrusions extending from the surface, wherein the improvement comprises:
    the microprotrusions having an average height greater than about 10 microns;
    at least a portion of the surface, microprotrusions, or combinations thereof coated with an adhesive glue,
    wherein the adhesive glue coating has a thickness of less than 75% of the average height of the protrusions; and
    wherein the 90° pull off adhesive strength of the article is at least about $1.0 N/cm^2$.

2. The article of claim 1, wherein the substrate comprises one or more biodegradable materials, one or more non-biodegradable materials, or combinations thereof.

3. The article of claim 2, wherein the one or more biodegradable materials is selected from the group consisting of aliphatic polyesters, poly(amino acids), poly(ether-esters), polyalkylene oxalates, poly(carbonates), poly(iminocarbonates), poly(ortho esters), poly(oxaesters), poly(amidoesters), poly(anhydrides), polyphosphazenes, poly(lactic-co-glycolic acid) (PLGA), polycaprolactone (PCL), polyglycolide (PGA), polylactic acid (PLA), poly-3-hydroxybutyrate (PHB), star-poly-caprolactone-co-D,L-lactide, poly(tri-methyl carbonate-co-caprolactone), poly(ethylene glycol) (PEG), polyurethanes, parylene-C, poly(citric-diol), hyaluronic acid, collagen, elastin, laminin, gelatin, chondroitin sulfate, dextran, chitosan, alginate, keratin, agrose, or combinations thereof.

4. The article of claim 2, wherein the one or more non-biodegradable materials is selected from the group consisting of acrylics, butyl rubber, ethyl vinyl acetate, poly(amide imides), poly(etherketones), polycarbonates, polyolefins, such as polyethylenes and polypropylenes, polybutylene terephthalates, polydimethylsiloxane (PDMS), polyethylene terephthalates, polyamides, polyvinylidene fluoride, polyacrylates, such as polymethylmethacrylate and polyhydroxyethylmethacrylate, polyacrylamides, such as poly(N-isopropylacrylamide), polyvinylalcohols, and combinations thereof.

5. The article of claim 2, wherein the substrate is biodegradable in whole or in part.

6. The article of claim 5, wherein the substrate comprises in whole or in part polycaprolactone.

7. The article of claim 1, wherein the 90° pull off adhesive strength of the article is at least about $1.25 N/cm^2$.

8. The article of claim 1, wherein the microprotrusions have a height between about 11 to about 20 microns.

9. The article of claim 8, wherein the height of the microprotrusions is about 19 microns.

10. The article of claim 1, wherein the microprotrusions have a base diameter between about 3 microns to about 7 microns.

11. The article of claim 10, wherein the base diameter of the microprotrusions is about 5 microns.

12. The article of claim 1, wherein the center-to-center distance between the microprotrusions is between about 5 microns to about 20 microns.

13. The article of claim 1, wherein the aspect ratio of the microprotrusions is less than 7.

14. The article of claim 1, wherein the adhesive glue is selected from the group consisting of cyanoacrylates, aldehyde adhesives, acrylate adhesives; urethane adhesives; hydroxysuccinimide adhesives, catechol-containing adhesives, and combinations thereof.

15. The article of claim 14, wherein the adhesive glue comprises a cyanoacrylate.

16. The article of claim 1, wherein the adhesive glue coating thickness at the base of the microprotrusions is between about 1 micron to about 5 microns.

17. The article of claim 16, wherein the coating thickness is about 2.5 microns.

18. The article of claim 1, wherein the 90° pull off adhesive strength is at least about 1.75 N/cm$^2$.

19. The article of claim 1, wherein the article is biocompatible.

20. The article of claim 1, wherein the article is a tape or patch.

21. The article of claim 1, wherein the article further comprises a sacrificial layer that is coated on top of the adhesive to protect the adhesive layer prior to application.

22. The articles of claim 1, wherein the article further comprises one or more therapeutic agents, prophylactic agents, diagnostic agents, nutraceuticals, or combinations thereof.

23. A method comprising contacting the article of claim 1 to a tissue.

24. The method of claim 23, wherein the tissue is contacted in viva.

25. A method comprising contacting the article of claim 1 to a medical device.

26. The article of claim 1, wherein the thickness of the coating is less than 50% of the height of the protrusions.

27. The article of claim 1, wherein the thickness of the coating is less than 25% of the height of the protrusions.

28. The article of claim 1, wherein the 90° pull off adhesive strength of the article is at least about 1.5 N/cm$^2$.

* * * * *